United States Patent
Ganeshananthan et al.

(10) Patent No.: US 11,107,572 B1
(45) Date of Patent: Aug. 31, 2021

(54) CROSS-VALIDATION OF DATA DERIVED FROM IMAGES CAPTURED DURING DIAGNOSTIC SESSIONS

(71) Applicant: Verily Life Sciences LLC, Mountain View, CA (US)

(72) Inventors: Rohan Ganeshananthan, San Francisco, CA (US); Brian Levinstein, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 16/828,159

(22) Filed: Mar. 24, 2020

Related U.S. Application Data

(60) Provisional application No. 62/823,368, filed on Mar. 25, 2019.

(51) Int. Cl.
  *G06K 9/00* (2006.01)
  *G16H 30/40* (2018.01)
  *G16H 30/20* (2018.01)
  *G06K 9/62* (2006.01)

(52) U.S. Cl.
  CPC .......... *G16H 30/40* (2018.01); *G06K 9/6215* (2013.01); *G06K 9/6267* (2013.01); *G16H 30/20* (2018.01)

(58) Field of Classification Search
  CPC ...... G16H 30/40; G16H 30/20; G06K 9/6215; G06K 9/6267
  See application file for complete search history.

(56) References Cited

U.S. PATENT DOCUMENTS

| | | | |
|---|---|---|---|
| 7,563,025 B2 | 7/2009 | Kay | |
| 2020/0035338 A1* | 1/2020 | Benson | A61B 34/10 |
| 2020/0113524 A1* | 4/2020 | Benson | A61B 5/4566 |
| 2020/0160997 A1* | 5/2020 | Bagci | G16H 70/60 |
| 2020/0161005 A1* | 5/2020 | Lyman | G06T 5/50 |

FOREIGN PATENT DOCUMENTS

EP  1400909 A1  3/2004

OTHER PUBLICATIONS

Coatrieux, Gouenou , et al., "Watermarking Medical Images with Anonymous Patient Identification to Verify Authenticity", eHealth Beyond the Horizon—Get IT There; IOS Press, Montreal, Canada; 2008 Organizing Committee of MIE; 7 pages., May 15, 2014.

(Continued)

*Primary Examiner* — Xin Jia
(74) *Attorney, Agent, or Firm* — Perkins Coie LLP

(57) ABSTRACT

Introduced here are diagnostic platforms able to verify subjects included in images in a time- and resource-efficient manner. By assessing the degree of consistency between multiple characterizations of an attribute that are derived from different data, a diagnostic platform can determine the likelihood that an image includes a given subject. An attribute could be characterized based on metadata that accompanies an image captured during a diagnostic session, information provided by an individual as part of the diagnostic session, an output produced by a classification model upon being applied to the image, or any combination thereof.

25 Claims, 10 Drawing Sheets

(56) References Cited

OTHER PUBLICATIONS

Pan, W., et al., "Medical Image Integrity Control Combining Digital Signature and Lossless Watermarking", Institut Telecom; Telecom Bretagne; France; Jan. 14, 2010; 12 pages., Jan. 14, 2010.
Tan, Chun Kiat, et al., "Security Protection of DICOM Medical Images Using Dual-Layer Reversible Watermarking with Tamper Detection Capability", Journal of Digital Imaging, vol. 24, No. 3 Jun. 2011: Singapore; pp. 528-540, Jun. 2011.

\* cited by examiner

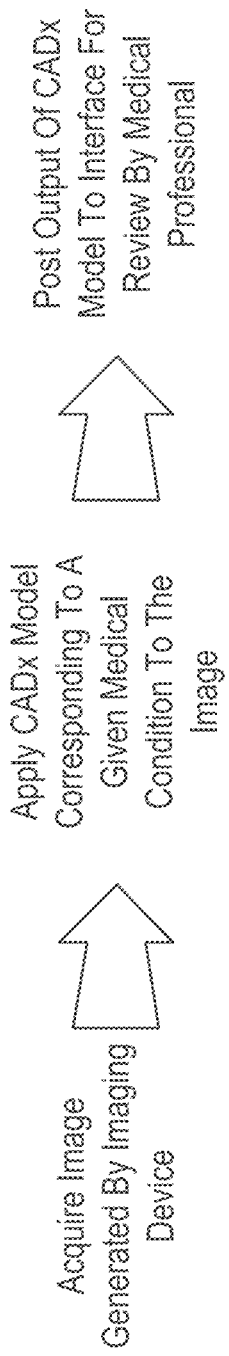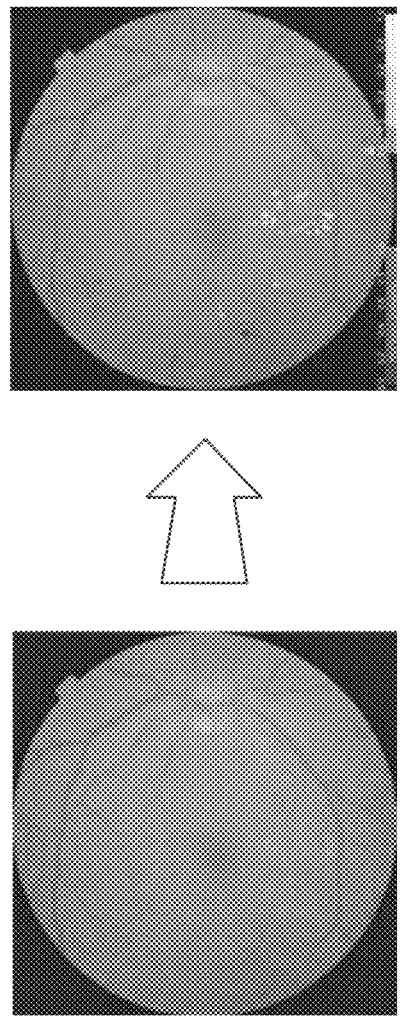
FIGURE 1

800

801

Acquire a first image and accompanying first data that specifies at least one attribute of a first diagnostic session

802

Apply a classification model to the first image to produce a first characterization of an attribute of a first individual included in the first image

803

Populate a first record to associate the first image and the first characterization with at least a portion of the accompanying first data

804

Acquire a second image and accompanying second data that specifies at least one attribute of a second diagnostic session

805

Apply the classification model to the second image to produce a second characterization of the attribute of a second individual included in the second image

806

Compare the first and second characterizations of the attribute to determine whether the first and second individuals are the same individual

807

Determine that the first and second individuals are the same individual

808

Populate a second record to associate the second image with the first image

FIGURE 8

CROSS-VALIDATION OF DATA DERIVED FROM IMAGES CAPTURED DURING DIAGNOSTIC SESSIONS

CROSS-REFERENCE TO RELATED APPLICATIONS

This application claims priority to U.S. Provisional Application No. 62/823,368, titled "Cross-Validation of Data Derived from Images Captured During Diagnostic Sessions" and filed on Mar. 25, 2019, which is incorporated by reference herein in its entirety.

TECHNICAL FIELD

Various embodiments concern computer programs and associated computer-implemented techniques for assessing the degree of consistency between multiple characterizations of an attribute related to a diagnostic session.

BACKGROUND

The process by which visual representations of a human body are captured is referred to as "medical imaging" or "biological imaging." Generally, medical imaging seeks to reveal internal structures hidden by the skin or bones in order to detect the presence of a disease. For example, a series of digital images (or simply "images") corresponding to different aspects of the anatomy of the human body may make it possible to more readily identify abnormalities.

A variety of different technologies may be used to capture these images. Examples of such technologies include x-ray, magnetic resonance imaging (MRI), ultrasonography or ultrasound, endoscopy, microscopy, elastography, tactile imaging, thermography, computed tomography (CT), fluoroscopy, angiography, mammography, positron emission tomography (PET), single photon emission computed tomography (SPECT), and the like. The ever-growing number of images (as well as the need to share these images) requires that the subjects included in these images be accurately identified.

BRIEF DESCRIPTION OF THE DRAWINGS

Various features of the technology will become more apparent to those skilled in the art from a study of the Detailed Description in conjunction with the drawings. Embodiments of the technology are illustrated by way of example and not limitation in the drawings, in which like references may indicate similar elements.

FIG. 1 illustrates an example scenario in which a diagnostic platform acquires a retinal image generated by a fundus camera, applies a computer-aided diagnostic (CADx) model corresponding to a given ailment to the retinal image, and then posts an output produced by the CADx model to an interface for review by a medical professional.

FIG. 8 depicts a flow diagram of a process for discovering the likelihood that an image captured during a diagnostic session is related to a subject who was included in another image capturing during a previous diagnostic session.

Figure 2A:
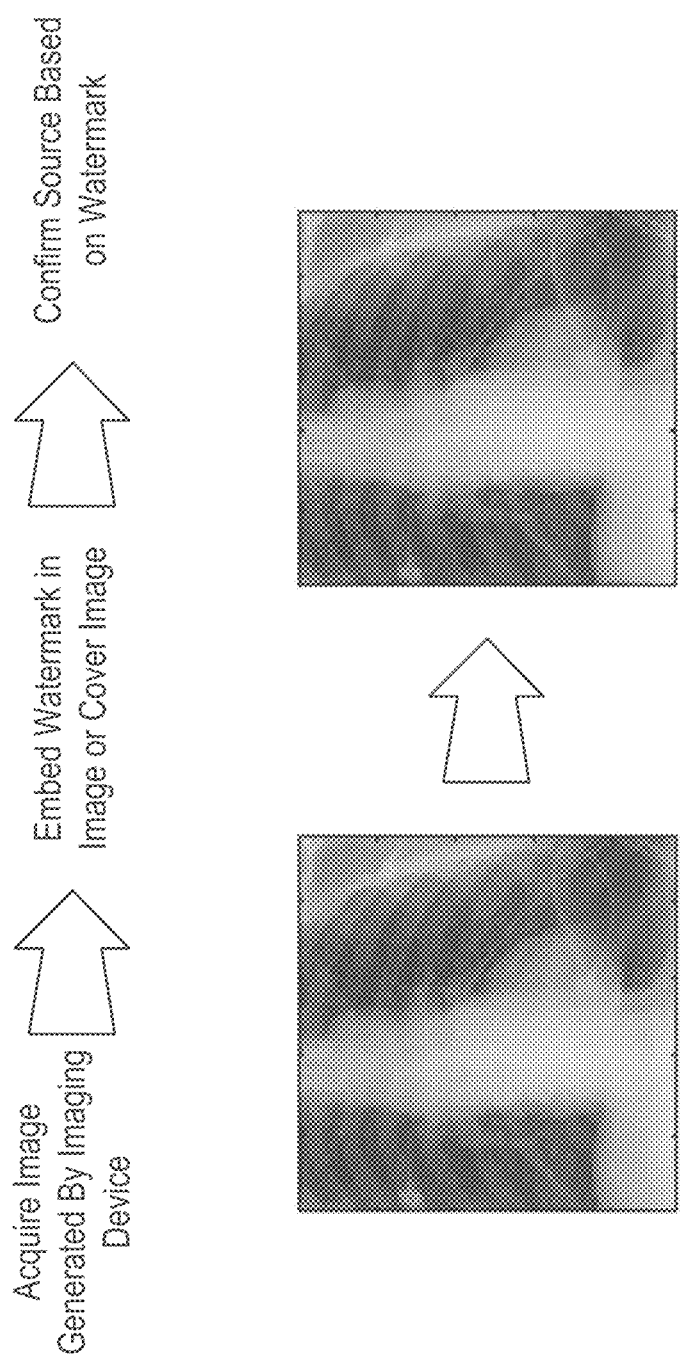
FIG. 2A depicts a high-level flow diagram of an example process for embedding a watermark within an image.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Imaging has historically been the most effective means for detecting a variety of ailments. For example, radiological imaging has been shown to be the most effective means for early detection of breast cancer and diabetic retinopathy (DR), among other ailments. However, differentiating the features in an image can be difficult. For instance, the differences between benign and malignant growths may be largely indistinguishable to the human eye.

Accordingly, computer-aided diagnosis technologies have become a part of routine clinical work in several areas of medicine. To increase the accuracy of image interpretation, a diagnostic platform can apply one or more computer-aided diagnostic (CADx) models to an image. FIG. 1 illustrates an example scenario in which a diagnostic platform acquires a retinal image generated by a fundus camera, applies a CADx model corresponding to a given ailment to the retinal image, and then posts an output produced by the CADx model to an interface for review by a medical professional. In some instances the output is a proposed diagnosis with respect to the given ailment, while in other instances the output is intended to facilitate the rendering of a diagnosis. For example, the output may include an image in which the feature(s) determined to be diagnostically relevant by the diagnostic platform have been visually highlighted in some manner.

In general, each CADx model is designed to apply algorithm(s) to an image to produce an output that conveys information about a corresponding ailment or disease (collectively referred to as "medical conditions"). The output is normally considered as a "second opinion" by the medical professional responsible for interpreting the image. Thus, CADx models can act as decision aids for medical professionals (e.g., radiologists and ophthalmologists) in characterizing the features of an image.

Attributing an image to the wrong subject, however, can have significant, irreversible effects. For instance, a subject suffering from an ailment may remain in an undiagnosed, and thus untreated, state. Therefore, confirming the identity of subjects included in images is a critical part of the diagnostic process. Diagnostic platforms have historically confirmed the identities of subjects based on either watermarks embedded in images or metadata that accompanied the images.

Watermarks have traditionally been embedded in images to identify the subject included in an image in a private manner. FIG. 2A depicts a high-level flow diagram of an example process for embedding a watermark within an image. In such a process, watermark information can be directly embedded in the image (e.g., by changing pixel values) or a cover image designed to overlay the image. Some watermarks are readily visible, while other watermarks may be largely invisible. But watermarking suffers from several downsides. First, it can be difficult to embed a meaningful watermark without compromising the quality of the image. Second, it can be difficult to embed confidential information in the image that can be retrieved without error after the image has been altered (e.g., due to decompression or shifting of hues, contrast, etc.).

Figure 2B:
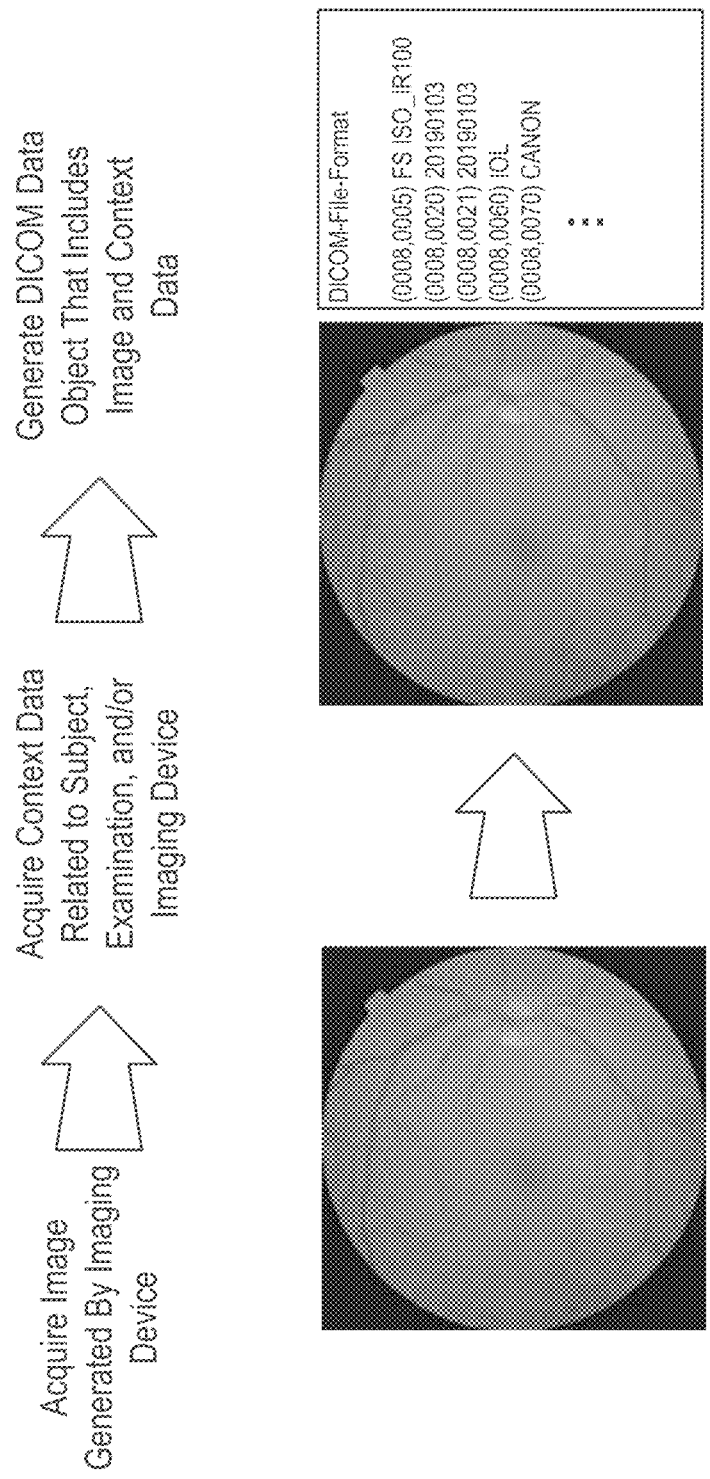
FIG. 2B depicts a flow diagram of an example process for generating metadata for a retinal image produced by a fundus camera (also referred to as a "retinal camera") during a diagnostic session.

In contrast to watermarks, metadata can provide considerable information regarding the diagnostic session in which an image was generated. FIG. 2B depicts a flow diagram of an example process for generating metadata for a retinal image produced by a fundus camera (also referred to as a "retinal camera") during a diagnostic session. While the example process is described in the context of a Digital Imaging and Communications in Medicine (DICOM) data object, those skilled in the art will recognize that the example process is similarly applicable to other formats. Similarly, while the example process is described in the context of a retinal image, those skilled in the art will recognize that the example process is similarly applicable to images of other parts of the human body.

Initially, the retinal camera will generate an image of the retinal of a human body. Images generated during diagnostic sessions will often include one or more physiological structures of interest, rather than the entirety of the human body. For example, a retinal image may depict the retina, optic disk, and blood vessels within the eye. Thereafter, a DICOM data object can be created that includes pixel data of the retinal image and contextual metadata (also referred to as "context data") specifying attribute(s) of the diagnostic session. Such action may be performed by the retinal camera or some other electronic device (e.g., a computer server accessible to the retinal camera across a network). Thus, in some instances, the retinal camera may need to transmit the retinal image to the other electronic device before the DICOM data object is created.

The DICOM format causes information related to diagnostic sessions to be grouped into data sets. For example, a DICOM data object (also referred to as a "DICOM file") can include attribute(s) in the form of context data and one special attribute that contains pixel data. Thus, a DICOM data object that includes a retinal image may contain an identifier for the subject whose retina was imaged so that this information cannot be separated from the retinal image by mistake. Computer programs designed to handle DICOM data objects must be able to parse the information to discover the attribute(s) and the special attribute. Generally, a computer program accomplishes this by identifying tags represented by hexadecimal digits enclosed by parentheses and separated by a comma. Each tag may be followed by a field that includes relevant information. By examining the tag, the computer program can determine what type of information is included in the field. For example, (0008, 0060) is the tag corresponding to the field for modality, while (0008,0070) is the tag corresponding to the manufacturer of the imaging device.

In practice, the DICOM format acts much like other image formats, such as JPEG, TIFF, or PNG, that embed tags within an image to convey information. Because the DICOM format requires that the pixel data and context data be written in a consistent format, DICOM data objects can be readily exchanged between two entities/devices without issue. Additional information on the DICOM format can be found in the DICOM Standard and its related publications as maintained by the Medical Imaging & Technology Alliance, a division of the National Electrical Manufacturers Association.

Despite extensive improvements to these solutions, images continue to be routinely associated with the wrong subjects. Introduced here, therefore, are diagnostic platforms able to verify the identity of subjects included in images in a time- and resource-efficient manner. By assessing the degree of consistency between multiple characterizations of an attribute that are derived from different data, a diagnostic platform can determine the likelihood that the data is related to a single diagnostic session (and thus a given subject). As further described below, an attribute could be characterized based on metadata that accompanies an image captured during a diagnostic session, information provided by an individual as part of the diagnostic session, an output produced by a classification model upon being applied to the image, or any combination thereof.

Because the diagnostic platform can consider consistency of characterizations separately determined based on unrelated data, the diagnostic platform can better identify, understand, and address potential discrepancies. For example, if the diagnostic platform discovers that the output produced by a classification model implies that the subject is male but the information provided by an individual (e.g., a medical professional) responsible for capturing the image specifies the subject is female, then the diagnostic platform may take additional action(s). As another example, if the diagnostic platform discovers that the output produced by a classification model implies that the subject is likely greater than 40 years old but the metadata that accompanies the image specifies the subject is 28 years old, then the diagnostic platform may take additional action(s).

Embodiments may be described with reference to particular medical conditions, imaging devices, computer programs, networks, etc. However, those skilled in the art will recognize that these features are similarly applicable to other medical conditions, imaging device types, computer program types, network types, etc. For example, although embodiments may be described in the context of classification models to be applied to retinal images generated by retinal cameras, the relevant features may be similarly applicable to classification models to be applied to images of other parts of the human body.

Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program a computing device to perform a process for acquiring pixel data for an image generated during a diagnostic session and context data specifying an attribute of the diagnostic session, applying a classification model to the pixel data to produce a first characterization of the attribute, producing a second characterization of the attribute based on the context data or information provided by an individual (e.g., the subject or a medical professional) during the diagnostic session, determining a degree of consistency between the first and second characterizations of the attribute, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

Figure 3:
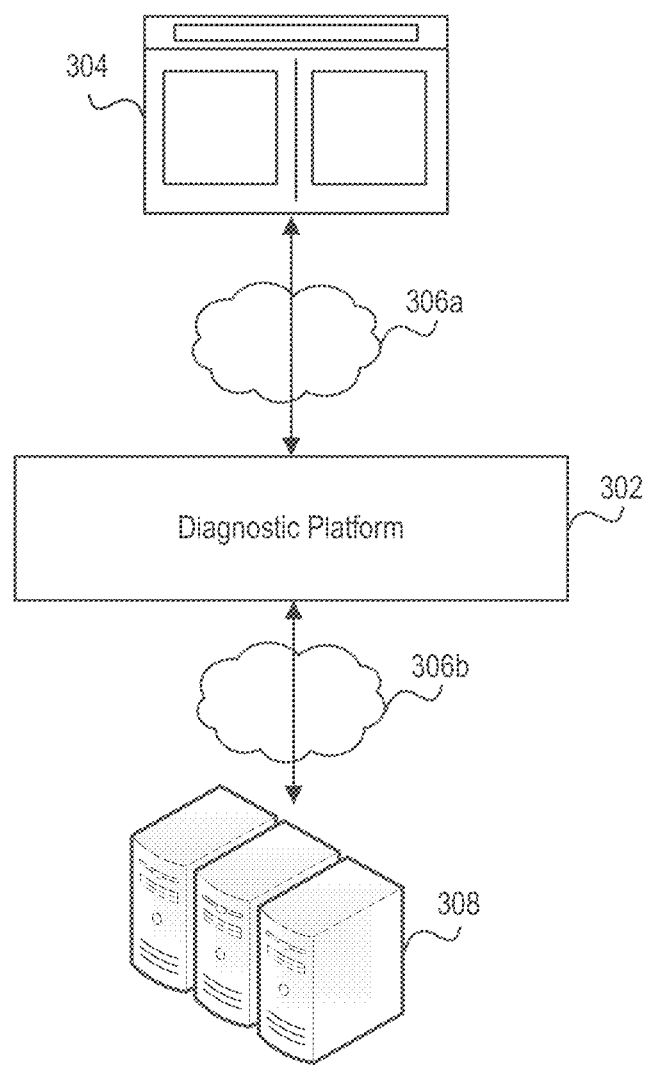
FIG. 3 illustrates a network environment that includes a diagnostic platform.

FIG. 3 illustrates a network environment 300 that includes a diagnostic platform 302. Individuals can interact with the diagnostic platform 302 via an interface 304. For example, medical professionals may access the interface 304 to review outputs produced by diagnostic models. The diagnostic platform 302 may be responsible for applying diagnostic models to images taken of subjects (also referred to as "patients") to identify the clinically- or diagnostically-relevant segment(s), generate records of the outputs produced by the diagnostic models, etc. When applied to an image produced by an imaging device, the diagnostic model may produce an output indicative of the health state of a corresponding subject. Examples of imaging devices include retinal cameras, x-ray generators and detectors, MRI machines, CT machines, digital cameras (e.g., digital single-lens reflex (DSLR) cameras and mirrorless cameras), etc.

Some diagnostic models produce proposed diagnoses that can be examined by a medical professional, while other diagnostic models produce a visualization component intended to help the medical professional render a diagnosis. For example, the application of a diagnostic model to the image may cause the segment(s) determined to be diagnostically relevant to be highlighted, outlined, etc. The term "health state" can refer to the physical health of the subject with respect to a given medical condition. For example, some diagnostic platforms are designed to identify/monitor digital features known to be indicative of diabetic retinopathy (DR), while other diagnostic platforms are designed to identify/monitor features in images known to be indicative of breast cancer.

However, the output produced by a diagnostic model is only relevant to the subject included in the image. Confirming the identity of subjects included in images, therefore, is a critical part of the diagnostic process. To validate an image, the diagnostic platform 302 may acquire/produce multiple characterizations of an attribute related to the diagnostic session in which the image was captured. As further described below, the attribute may be related to the subject, the imaging device responsible for generating the image, or the image itself. By assessing the degree of consistency between multiple characterizations of the attribute that are derived from different data, the diagnostic platform can determine the likelihood that an image includes a given subject (i.e., whether the image should be deemed "validated"). For example, if the degree of consistency between a pair of characterizations falls beneath a threshold, then the diagnostic platform 302 may cause display of a notification that specifies a potential discrepancy in the attribute, as separately and independently determined based on different data, exists.

As shown in FIG. 3, the diagnostic platform 302 may reside in a network environment 300. Thus, the diagnostic platform 302 may be connected to one or more networks 306a-b. The network(s) 306a-b can include personal area networks (PANs), local area networks (LANs), wide area networks (WANs), metropolitan area networks (MANs), cellular networks, the Internet, etc. Additionally or alternatively, the diagnostic platform 302 can be communicatively coupled to computing device(s) over a short-range communication protocol, such as Bluetooth® or Near Field Communication (NFC).

The interface 304 is preferably accessible via a web browser, desktop application, mobile application, or over-the-top (OTT) application. Accordingly, the interface 304 may be viewed on a personal computer, tablet computer, mobile workstation, mobile phone, game console, music player, wearable electronic device (e.g., a watch or fitness accessory), network-connected ("smart") electronic device, (e.g., a television or home assistant device), virtual/augmented reality system (e.g., a head-mounted display), or some other electronic device.

Some embodiments of the diagnostic platform 302 are hosted locally. That is, the diagnostic platform 302 may reside on the computing device used to access the interface 304. For example, the diagnostic platform 302 may be embodied as a mobile application executing on a mobile phone or a desktop application executing on a mobile workstation. Other embodiments of the diagnostic platform 302 are executed by a cloud computing service operated by Amazon Web Services® (AWS), Google Cloud Platform™, Microsoft Azure®, or a similar technology. In such embodiments, the diagnostic platform 302 may reside on a host computer server that is communicatively coupled to one or more content computer servers 308. The content computer server(s) 308 can include images to be examined for the purpose of rendering diagnoses, subject information (e.g., age, sex, health diagnoses, etc.), imaging device information (e.g., resolution, expected file size, etc.), diagnostic models, classification models, and other assets. Such information could also be stored on the host computer server.

Certain embodiments are described in the context of network-accessible interfaces. However, those skilled in the art will recognize that the interfaces need not necessarily be accessible via a network. For example, a computing device may be configured to execute a self-contained computer program that does not require network access. Instead, the self-contained computer program may cause necessary assets (e.g., images, diagnostic models, classification models, or processing operations) to be downloaded at a single point in time or on a periodic basis (e.g., weekly, daily, or hourly).

Figure 4:
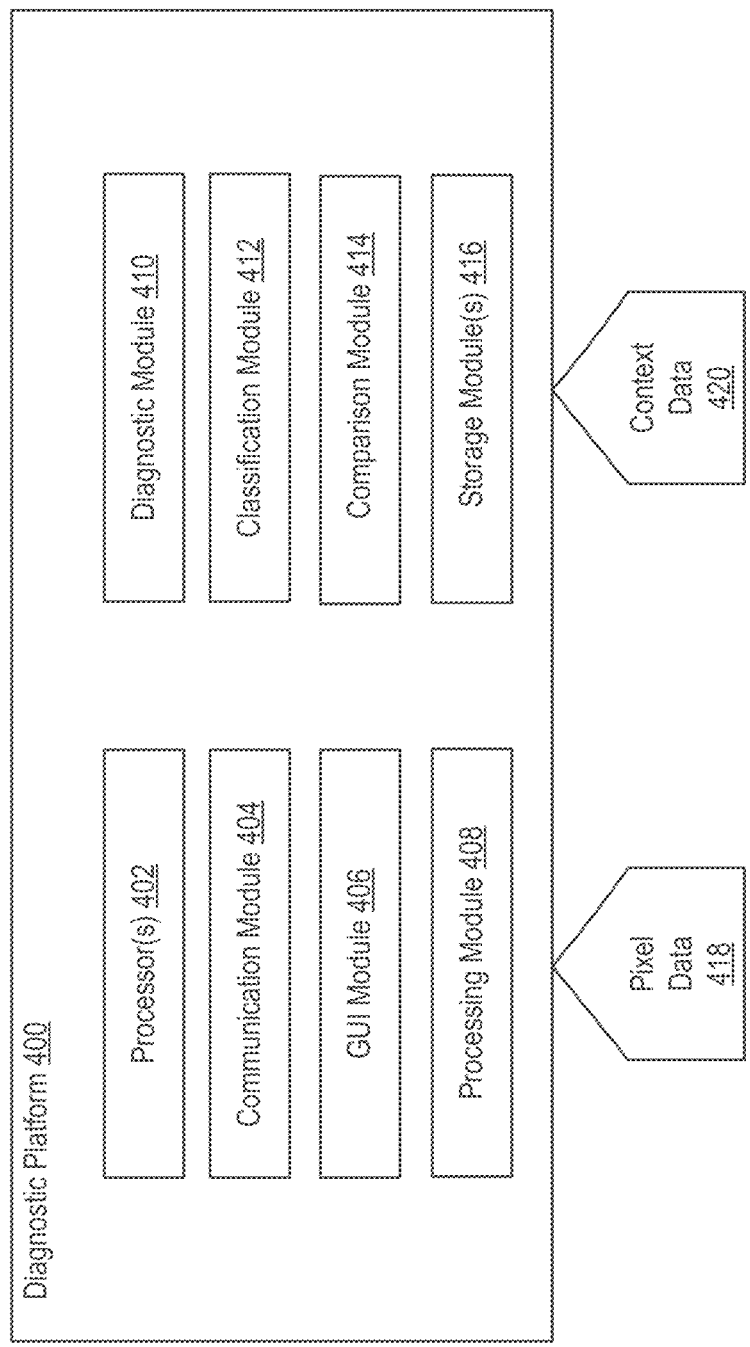
FIG. 4 depicts the high-level architecture of a diagnostic platform able to assess the degree of consistency between multiple characterizations of an attribute related to a diagnostic session in which an image is captured.

FIG. 4 depicts the high-level architecture of a diagnostic platform 400 able to assess the degree of consistency between multiple characterizations of an attribute related to a diagnostic session in which an image is captured. Such action enables the diagnostic platform 400 to determine the likelihood that the image includes a given subject. For instance, if the diagnostic platform 400 discovers that at least two characterizations are consistent with one another (e.g., by being substantially identical), then the diagnostic platform 400 may validate the image. However, if the diagnostic platform 400 discovers that at least two characterizations are inconsistent with one another, then the diagnostic platform 400 may take additional action(s). For example, the diagnostic platform 400 may take further action. For instance, the diagnostic platform 400 may cause a notification to be shown on an interface (e.g., interface 304 of FIG. 3).

The diagnostic platform 400 can include one or more processors 402, a communication module 404, a graphical user interface (GUI) module 406, a processing module 408, a diagnostic module 410, a classification module 412, a comparison module 414, and one or more storage modules 416. In some embodiments a single storage module includes multiple computer programs for performing different operations (e.g., metadata extraction, image processing, digital feature analysis), while in other embodiments each computer program is hosted within a separate storage module. Embodiments of the diagnostic platform 400 may include some or all of these components, as well as other components not shown here.

The processor(s) 402 can execute modules from instructions stored in the storage module(s) 416, which can be any device or mechanism capable of storing information. For example, the processor(s) 402 may execute the GUI module 406, processing module 408, diagnostic module 410, classification module 412, or comparison module 414.

The communication module 404 can manage communications between various components of the diagnostic platform 400. The communication module 404 can also manage communications between the computing device on which the diagnostic platform 400 resides and another computing device.

For example, the diagnostic platform 400 may reside on a mobile workstation in the form of a desktop application. In such embodiments, the communication module 404 can facilitate communication with a network-accessible computer server responsible for supporting the desktop application and/or an imaging device responsible for generating images of subjects. The communication module 404 may facilitate communication with various data sources through the use of application programming interfaces (APIs), bulk data interfaces, etc. Examples of data sources include network-accessible databases, other desktop applications residing on the mobile workstation, etc.

As another example, the diagnostic platform 400 may reside on a server system that includes one or more network-accessible computer servers. In such embodiments, the communication module 404 can communicate with a computer program executing on a computing device accessible to an individual, such as a mobile phone, desktop computer, or mobile workstation. For example, a medical professional may review comparison measures (also referred to as "similarity measures" or "consistency measures") produced by the comparison module 414 by interacting with the diagnostic platform 400 via a web browser. As another example, the medical professional may review outputs produced by diagnostic models applied by the diagnostic module 410 or classification models applied by the classification module 412 via the web browser. Those skilled in the art will recognize that the components of the diagnostic platform 400 can be distributed between the server system and the computing device in various manners. For example, some data (e.g., images of subjects) may reside on the computing device for privacy purposes, while other data (e.g., processing operations for examining pixel data, producing characterizations based on the pixel data, and building subject profiles) may reside on the server system.

The GUI module 406 can generate the interface(s) through which an individual can interact with the diagnostic platform 400. For example, an interface may include an image of a body part that includes one or more digital features (e.g., highlighted segments or outlined segments) intended to assist in rendering a diagnosis with respect to a given medical condition. As another example, an interface may include information regarding characterizations of an attribute related to a diagnostic session in which an image was created.

The processing module 408 can apply operation(s) to pixel data 418 and/or context data 420 acquired by the diagnostic platform 400. In some embodiments, the pixel data 418 and the context data 420 are acquired from the same source. For example, the diagnostic platform 400 may be configured to acquire DICOM data objects, each of which includes pixel data 418 corresponding to an image generated during a diagnostic session and context date 420 specifying an attribute of the diagnostic session. In such embodiments, upon receiving a DICOM data object, the processing module 408 may parse the context data 420 to discover a characterization of an attribute related to the subject captured in the image, the imaging device responsible for generating the image, or the image itself.

In other embodiments, the pixel data 418 and the context data 420 are acquired from different sources. For example, the diagnostic platform 400 may be configured to acquire context data 420 from a network-accessible storage medium. The context data 420 may be representative of information provided by an individual as part of a diagnostic session. The individual may be the subject (who may have provided the information as part of an intake procedure) or the medical professional (who may have provided the information over the course of the diagnostic session). In such embodiments, if the pixel data 418 is acquired in the form of a DICOM data object, context data may be acquired from multiple sources (e.g., the DICOM data object and the network-accessible storage medium), though the different information may be provided by each context data.

Examples of sources include the computing device on which the diagnostic platform 400 resides, an imaging device to which the computing device is connected, and a network-accessible storage medium to which the computing device is connected. Different types of images may be acquired by the diagnostic platform 400 from multiple sources (e.g., different imaging devices). For example, the diagnostic platform 400 could acquire two-dimensional (2D) images, three-dimensional (3D) images, colored images, grayscale images (e.g., those captured during a fluorescein angiography procedure), etc. Thus, the processing module 408 may apply operation(s) to ensure that pixel data 418 received from multiple sources is in a compatible format that can be processed by the other modules.

A source may be configured to continuously or periodically transmit pixel data 418 and/or context data 420 to the diagnostic platform 400. In some embodiments, the source continually uploads data to the diagnostic platform 400 so long as the source remains communicatively coupled to the computing device on which the diagnostic platform 400 resides (e.g., via a Bluetooth® communication channel). For example, pixel data 418 may be streamed from the source to the diagnostic platform 400 in real time as images are generated. In other embodiments, the source uploads data to the diagnostic platform 400 on a periodic basis (e.g., hourly, daily, or weekly). For example, context data 420 corresponding to information provided by an individual (e.g., a medical profession) over the course of several diagnostic sessions may be delivered in a single batch to the diagnostic platform 400. In such embodiments, the processing module 408 may parse the context data 420 to identify which subset(s) correspond to each image represented by the pixel data 418. The diagnostic platform 400 can be configured to pull pixel data 418 and/or context data 420 from the source. Additionally or alternatively, the source can be configured to push pixel data 418 and/or context data 420 to the diagnostic platform 400. In some embodiments, an individual (e.g., an administrator or a medical professional) is able to configure these push/pull settings. These settings can be configured on a source-by-source basis.

After acquiring pixel data 418 corresponding to an image, the diagnostic module 410 can identify an appropriate diagnostic model to apply to the image. Generally, the diagnostic model is one of multiple diagnostic models maintained in a library stored in the storage module(s) 416, and each diagnostic model may be associated with a different medical condition. The diagnostic model can include algorithm(s) that, when applied to the pixel data 418, produce an output that conveys information about a medical condition. For example, if the pixel data 418 corresponds to a retinal image generated by a retinal camera, the output of the diagnostic model may provide information regarding an eye-related medical condition such as diabetes, age-macular degeneration (AMD), glaucoma, neoplasm, DR, etc. The output is normally considered as a "second opinion" by the medical professional responsible for interpreting the image.

Computer-aided diagnosis technologies have become a part of routine clinical work in several areas of medicine. Attributing an image to the wrong subject, however, can have significant, irreversible effects. For instance, a subject suffering from an ailment may remain in an undiagnosed, and thus untreated, state. Therefore, confirming the identity of subjects included in images is a critical part of the diagnostic process. As further described below, one way to determine the likelihood that an image includes a given subject is to assess the degree of consistency between multiple characterizations of an attribute related to a diagnostic session in which the image was captured. That is, the likelihood that the image includes the given subject could be inferred based on the degree of contrast between multiple characterizations of the attribute, where the degree of contrast may be indicative of similarity or dissimilarity.

The diagnostic platform 400 can characterize or describe an attribute in several different ways.

First, if the diagnostic platform acquires a DICOM data object, the processing module 408 may parse context data included in the DICOM data object to discover a first characterization of the attribute. In such embodiments, the characterization is derived from the context data that accompanies the DICOM data object.

Second, the processing module 408 may parse information provided by an individual as part of a diagnostic session to establish a second characterization of the attribute. In some embodiments, the individual is the subject, who may have provided the information as part of an intake procedure. In other embodiments, the individual is the medical professional responsible for managing the diagnostic session, and who may have provided the information over the course of the diagnostic session (e.g., in the form of notes). In some instances, the processing module 408 may be able to establish separate characterizations based on information provided by the subject and the medical professional.

Third, the classification module 412 can apply a classification model to pixel data to produce a third characterization of the attribute. As further described below, the classification module 412 can initially identify an appropriate classification model to apply to the image based on the attribute. Generally, the classification model is one of multiple classification models maintained in another library stored in the storage module(s) 416, and each classification model may be associated with a different attribute. Thus, each classification model in the library can be designed to produce a characterization of a distinct attribute when applied to pixel data. The classification model can include algorithm(s) that, when applied to the pixel data 418, produce an output indicative of a characterization of an attribute.

Thereafter, the comparison module 414 can compute either a degree of consistency or a degree of similarity between these characterizations. A higher degree of similarity generally corresponds to a higher likelihood that multiple characterizations of an attribute are substantially identical. For example, multiple characterizations may indicate that the subject is female, that the imaging device has a particular resolution, etc. A higher degree of consistency, meanwhile, generally corresponds to a higher likelihood that multiple characterizations of an attribute are consistent with one another. For example, a first characterization may indicate that the subject is 30-40 years old while a second characterization may indicate that the subject is 34 years old. As another example, a first characterization may indicate that the subject is likely pregnant while a second characterization may indicate that the subject is female.

By comparing the degree of similarity/consistency to a threshold, the comparison module 414 can determine whether an image should be validated. Assume, for example, that a first characterization of an attribute is produced by the classification module 412 based on pixel data and a second characterization of the attribute is produced by the processing module 408 based on context data. In such embodiments, a lower degree of similarity/consistency is representative of a higher likelihood that the pixel data and the context data are related to different diagnostic sessions, different imaging devices, or different subjects.

Several examples of models are provided below:

Binary Classification Models: The output of a binary classification model specifies one of two classes. Examples of such models include those that specify whether an image is associated with the left eye or right eye, whether an image is associated with a male or female, whether an individual included is an image is pregnant or not pregnant, etc.

Non-Binary Classification Models: The output of a non-binary classification model specifies one of at least three classes. An example of such a model is one that specifies whether an image is associated with a first type of imaging device (e.g., a retinal camera manufactured by Entity A), a second type of imaging device (e.g., a retinal camera manufactured by Entity B), or a third type of imaging device (e.g., a retinal camera manufactured by Entity C).

Regression Models: The output of a regression model is a single number (e.g., 34.5 years old) or an interval of numbers (e.g., 32-38 years old). An example of such a model is one that estimates the age of an individual based on the pixel data of an image of the individual. For instance, the model may specify whether an individual included in an image is 18-25 years old, 25-35 years old, 35-45 years old, etc. Regression models are generally associated with continuous variables, such as age, five-year major adverse cardiac event probability, etc.

Some attributes are difficult to determine, even with the assistance of algorithm-driven classification models. For instance, attributes such as age and gender can be difficult to predict with certainty. Thus, binary and non-binary classification models can also be "fuzzy" in nature. A "fuzzy" classification model may provide an indication of the degree of certainty with which it has established a characterization of an attribute. For example, a fuzzy binary classification model may specify that the individual included in an image is at least 70% likely to be female. As another example, a fuzzy non-binary classification model may specify that the individual included in an image is approximately 80% likely to be 25-35 years old and approximately 20% likely to be 35-45 years old. The comparison module 414 may consider the degree of certainty when comparing multiple characterizations of an attribute.

Whether the comparison module 414 computes a degree of consistency or a degree of similarity may depend on which type(s) of classification models are applied by the classification module 412. For example, characterizations produced by fuzzy classification models may be associated with degrees of consistency due to the imprecise outputs produced by these models. Conversely, binary classification models may be better suited for degrees of similarity. For example, if the diagnostic platform 400 is configured to produce multiple (non-fuzzy) characterizations of the same attribute, then the comparison module 414 may determine whether the multiple characterizations are substantially identical to one another.

However, this need not always be the case. For example, a first binary classification model may produce a first characterization that specifies whether the subject is pregnant or not pregnant and a second binary classification model may produce a second characterization that specifies whether the subject is male or female. In such an embodiment, the comparison module 414 may calculate a degree of consistency because the first and second binary classification models are associated with different attributes (e.g., pregnancy status and gender).

As noted above, the attribute(s) for which characterizations are produced by the diagnostic platform 400 is related to a diagnostic session in which an image is created. In some embodiments, the attribute is related to the subject captured in the image. The characterization of such an attribute may be representative of, for example, whether the image is of the left eye or right eye, whether the image is of the exterior surface or interior surface of the eye, whether the subject is male or female, an age of the subject, etc. In some embodiments, the attribute is related to the imaging device responsible for capturing the image. The characterization of such an attribute may be representative of, for example, a field of view, a digital effect (e.g., a notch or imperfection) indicative of a given imaging device model, a model of imaging device, etc. In some embodiments, the attribute is related to the image itself. The characterization of such an attribute may be representative of, for example, a resolution, a capture time (e.g., as evidenced by a timestamp), a color parameter (e.g., whether the image is in greyscale format, has hue/contrast limitations, etc.), etc.

Figure 5:
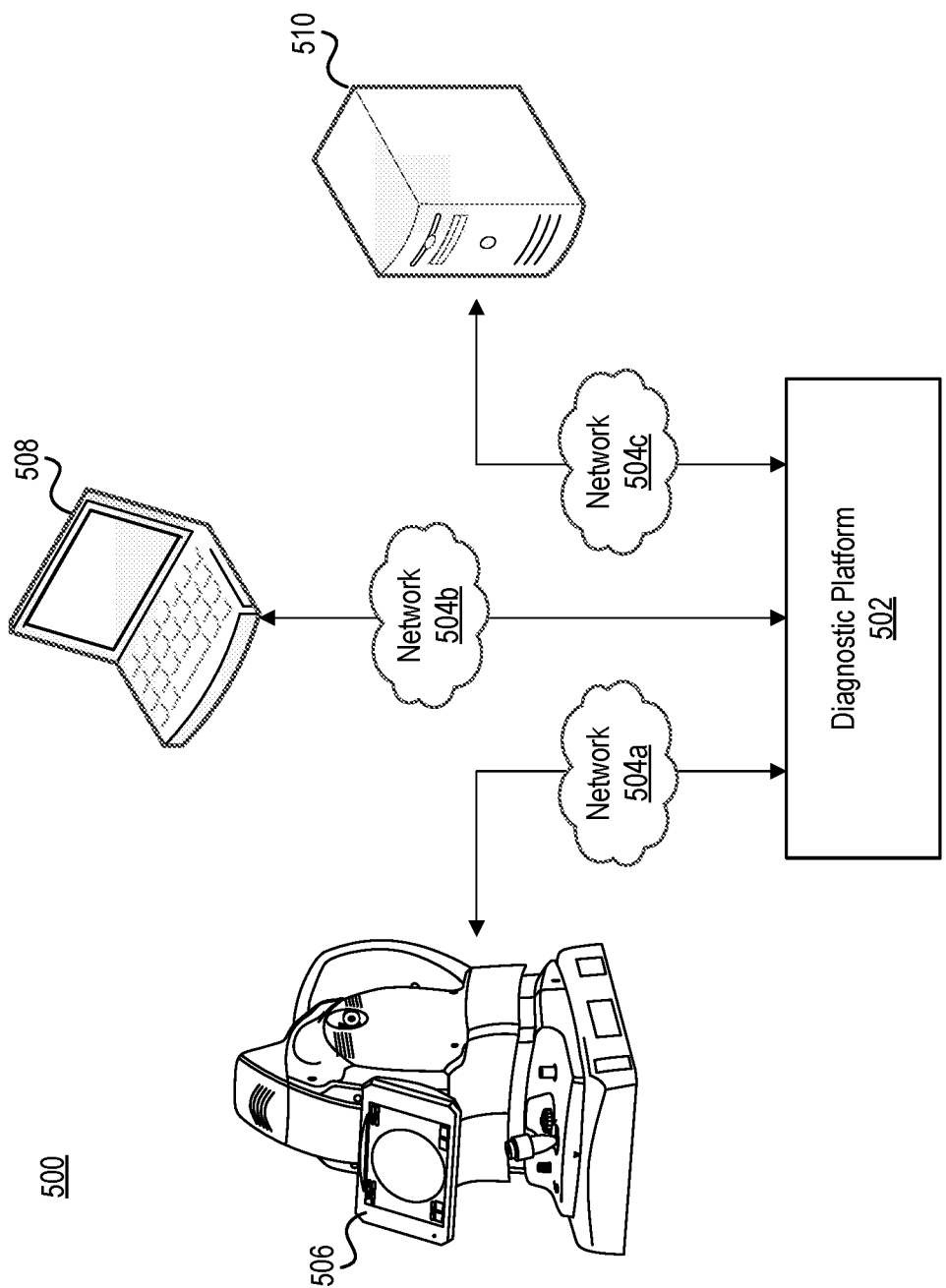
FIG. 5 depicts an example of a communication environment that includes a diagnostic platform configured to acquire data from one or more sources.

FIG. 5 depicts an example of a communication environment 500 that includes a diagnostic platform 502 configured to acquire data from one or more sources. Here, for example, the diagnostic platform 502 receives data from a retinal camera 506, laptop computer 508, and network-accessible server system 510 (collectively referred to as the "networked devices"). The data may include pixel data and/or context data.

The networked devices can be connected to the diagnostic platform 502 via one or more computer networks 504a-c. The computer network(s) 504a-c can include PANs, LANs, WANs, MANs, cellular networks, the Internet, etc. Additionally or alternatively, the networked devices may communicate with one another over a short-range communication protocol, such as Bluetooth® or Near Field Communication (NFC). For example, the diagnostic platform 502 resides on the network-accessible server system 510 in some embodiments. In such embodiments, data received from the network-accessible server system 510 need not traverse any computer networks. However, the network-accessible server system 510 may be connected to the retinal camera 506 and the laptop computer 508 via separate Wi-Fi communication channels.

Embodiments of the communication environment 500 may include some or all of the networked devices. For example, some embodiments of the communication environment 500 include a diagnostic platform 502 that receives pixel data and context data from the retinal camera 506 (e.g., in the form of DICOM data objects) and additional context data from the network-accessible server system 510 on which it resides. As another example, some embodiments of the communication environment 500 include a diagnostic platform 502 that receives pixel data from a variety of different retinal cameras located in different environments (e.g., different clinics).

Figure 6:
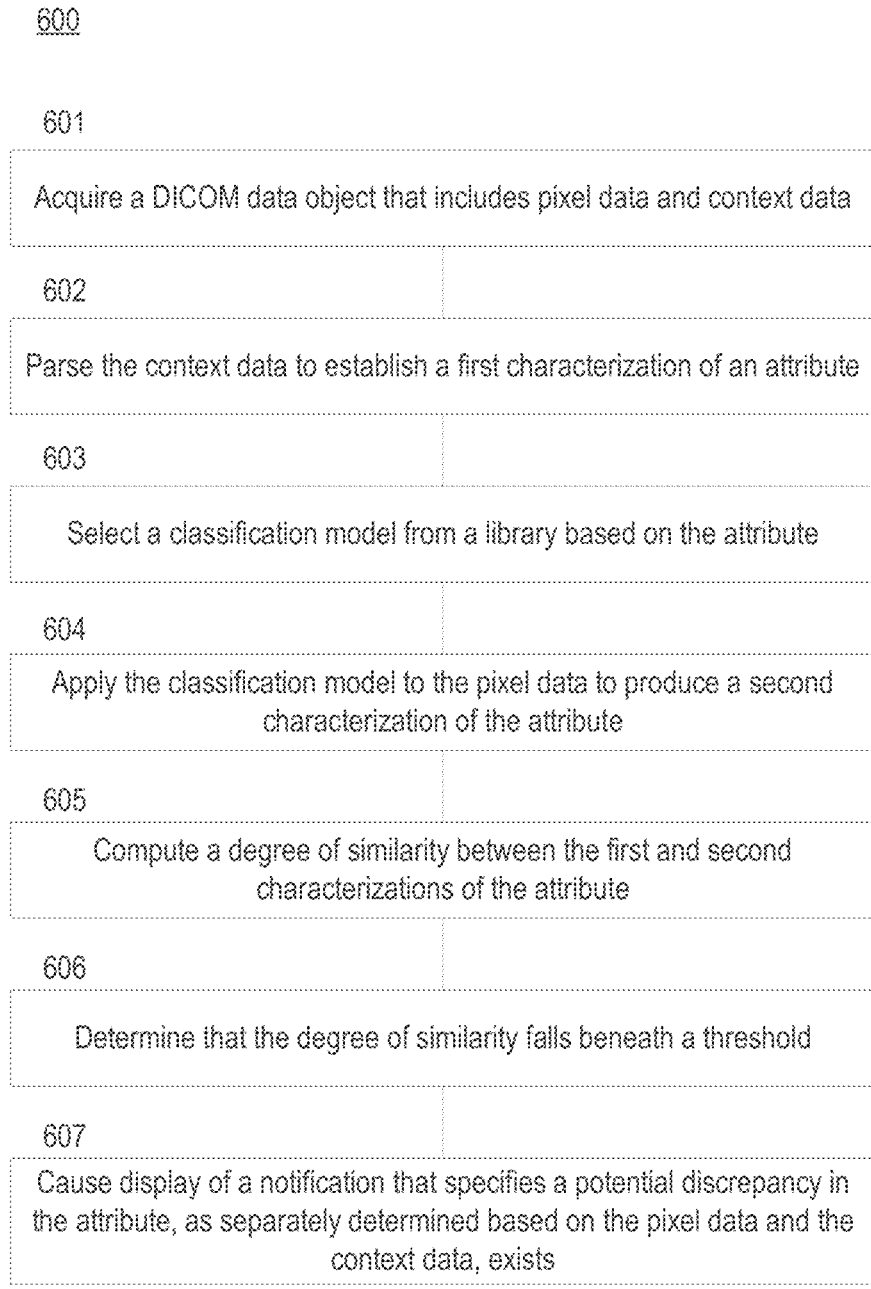
FIG. 6 depicts a flow diagram of a process for assessing the validity of an image captured during a diagnostic session.

FIG. 6 depicts a flow diagram of a process 600 for assessing the validity of an image captured during a diagnostic session. By assessing the validity, a diagnostic platform can determine whether the image is associated with a given subject. As noted above, such action may be critical if the diagnostic platform is also responsible for applying diagnostic model(s) to the image to assist in rendering diagnoses.

Initially, a diagnostic platform can acquire a DICOM data object that includes pixel data and context data (step 601). Generally, the pixel data corresponds to an image generated during a diagnostic session, while the context data specifies at least one attribute of the diagnostic session. The diagnostic platform can then parse the context data included in the DICOM data object to establish a first characterization of an attribute (step 602).

The diagnostic platform can select a classification model from a library based on the attribute (step 603), and then the diagnostic platform can apply the classification model to the pixel data to produce a second characterization of the attribute (step 604). In the process 600 of FIG. 6, the classification model corresponds to the attribute itself. Thus, the first and second characterizations are associated with the same attribute. For example, the first and second characterizations may each specify whether the subject is male or female, whether the image is related to the left eye or right eye, etc. However, in some embodiments, the classification model is associated with a related attribute rather than the attribute itself. For example, the first characterization may specify whether the subject is male or female, and the second characterization may specify whether the subject is pregnant or not pregnant. Although these characterizations relate to different attributes, the diagnostic platform can still determine whether a relationship exists between the pixel data and context data by comparing the first and second characterizations.

Thereafter, the diagnostic platform can compute a degree of similarity between the first and second characterizations of the attribute (step 605). For example, the diagnostic platform may compare the first and second characterizations of the attribute. Generally, a higher degree of similarity corresponds to a higher likelihood that the first and second characterizations are substantially identical to one another.

In some instances, the diagnostic platform will discover that the degree of similarity falls above a threshold. In such instances, the diagnostic platform may specify (e.g., in a digital record) that the image has been validated or take no further action. In other instances, the diagnostic platform will discover that the degree of similarity falls beneath the threshold (step 606). In such instances, the diagnostic platform may perform additional action(s). For example, the diagnostic platform may cause display of a notification that specifies a potential discrepancy in the attribute, as separately determined based on the pixel data and the context data, exists (step 607). The notification may be displayed on a computing device associated with an individual (e.g., a medical professional) responsible for reviewing outputs produced by the diagnostic platform.

Figure 7:
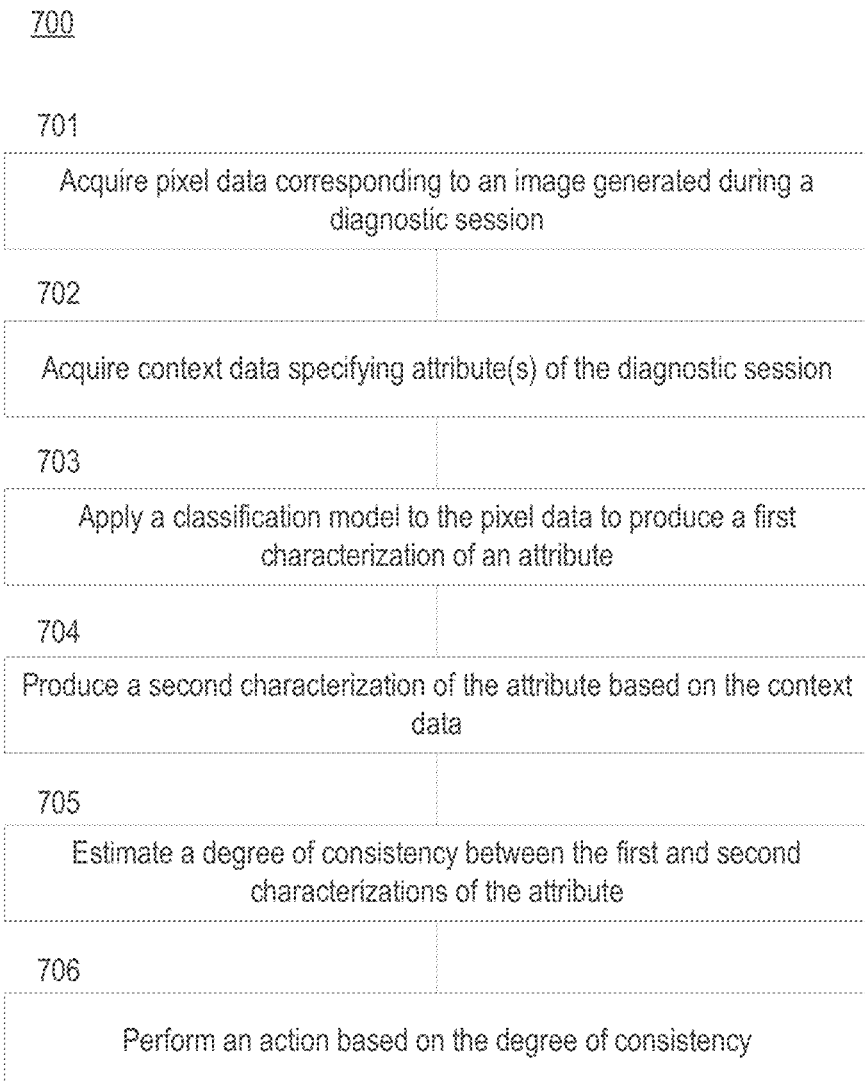
FIG. 7 depicts a flow diagram of another process for assessing the validity of an image captured during a diagnostic session.

FIG. 7 depicts a flow diagram of another process 700 for assessing the validity of an image captured during a diagnostic session. Initially, a diagnostic platform can acquire pixel data corresponding to the image (step 701), as well as context data specifying attribute(s) of the diagnostic session (step 702). In some embodiments, the pixel data and context data are acquired from the same source. For example, the context data may accompany the pixel data in the form of metadata (e.g., as part of a structured image format, such as DICOM, JPEG, etc.). In other embodiments, the pixel data and context data are acquired from separate sources. For example, the pixel data may be acquired, directly or indirectly, from the imaging device that captured the image, while the context data may be acquired from a network-accessible storage medium into which individuals (e.g., subjects or medical professionals) upload information provided as part of the diagnostic session.

The diagnostic platform can then apply a classification model to the pixel data to produce a first characterization of an attribute (step 703). As noted above, the classification model can include algorithm(s) that, when applied to the pixel data, produce an output that characterizes the attribute. In some embodiments, the classification model is one of multiple classification models maintained in a library accessible to the diagnostic platform, and each classification model may be associated with a different attribute.

Thereafter, the diagnostic platform can produce a second characterization of the attribute based on the context data (step 704). For example, the diagnostic platform may parse context data that accompanies the pixel data to discover a metadata element (also referred to as a "tag") that provides information regarding the attribute. As another example, the diagnostic platform may parse context data representative of information provided by an individual as part of the diagnostic session to discover information regarding the attribute. The individual may be the subject (who may have provided the information as part of an intake procedure) or a medical professional (who may have provided the information over the course of the diagnostic session).

The diagnostic platform can then estimate a degree of consistency between the first and second characterizations of the attribute (step 705). Generally, a higher degree of consistency corresponds to a higher likelihood that multiple characterizations of an attribute are consistent with one another. Moreover, the diagnostic platform can perform an action based on the degree of consistency (step 706). For example, responsive to discovering that the degree of consistency falls above a threshold (e.g., an upper threshold), the diagnostic platform may specify (e.g., in a digital record) that the image has been validated, cause display of a notification indicating that validation has been successful, or take no further action. As another example, responsive to discovering that the degree of consistency falls beneath a threshold (e.g., a lower threshold), the diagnostic platform may cause display of a notification that specifies a potential discrepancy in the attribute exists. Additionally or alternatively, the diagnostic platform may identify the potential discrepancy in a record associated with the image and then store the record in a log, which specifies the images that require further review to address potential discrepancies.

In some embodiments, the diagnostic platform determines which action(s), if any, are appropriate in accordance with a multi-tiered framework. For example, if the degree of consistency exceeds an upper threshold, the diagnostic platform may specify in a digital record associated with the image that no potential discrepancy was discovered. Moreover, if the degree of consistency falls beneath a lower threshold, the diagnostic platform may specify in the digital record that a potential discrepancy was discovered. Such action may prompt the display of a notification on a display accessible to, for example, a medical professional responsible for examining the image. However, if the degree of consistency falls between the upper and lower thresholds, the diagnostic platform may determine that further action is needed. For example, the diagnostic platform may compare multiple characterizations of another attribute (or pair of related attributes) to produce another degree of consistency. As another example, the diagnostic platform may surface an alert that indicates a validity determination cannot be reached.

Over time, the diagnostic platform may also examine feedback provided by individuals responsible for reviewing the outputs produced by the diagnostic platform. Such action allows the diagnostic platform to programmatically train itself (e.g., through the application of machine learning algorithms) to identify which attribute(s) are best suited for assessing the validity of images captured during diagnostic sessions. For instance, the diagnostic platform may discover that certain pairs of related attributes (e.g., pregnancy status and gender) are more consistently linked than others (e.g., age and stage of ocular degeneration).

The process 700 of FIG. 7 has been described in the context of a single attribute for the purpose of illustration only. Those skilled in the art will recognize that a similar process can be employed for characterizations of related attributes. For example, the diagnostic platform may be configured to estimate the degree of consistency between characterizations of pregnancy status and gender, camera model and image resolution, camera model and field of view (FOV), etc. As another example, the diagnostic platform may be configured to estimate the degree of consistency between the date of birth (e.g., as specified by the subject during intake), the image capture date, and the age as predicted by a regression model based on the pixel data of an image. In such embodiments, the diagnostic platform might determine whether the age is approximately equal to the image capture date minus the date of birth. As another example, the diagnostic platform may be configured to estimate the degree of consistency between different characterizations of an anatomical feature. By comparing these characterizations, the diagnostic platform may discover, for example, that a subject's medical history specifies they have had photocoagulation laser therapy but no visible laser scars have been detected in a retinal image allegedly associated with the subject. As another example, the diagnostic platform may be configured to estimate the degree of consistency between the image capture date/time as recorded in metadata accompanying an image and the diagnostic session date/time as recorded in another database (e.g., a calendar maintained by a clinic). As another example, the diagnostic platform may be configured to estimate the degree of consistency between the camera manufacturer specified in metadata accompanying an image and the camera manufacturer as predicted based on a defect present in the image (e.g., a notch located in a given quadrant).

FIG. 8 depicts a flow diagram of a process 800 for discovering the likelihood that an image captured during a diagnostic session is related to a subject who was included in another image capturing during a previous diagnostic session. While the process 800 is described in the context of an attribute of an individual, those skilled in the art will recognize that the process 800 is similarly applicable to digital features of images produced by imaging device. For example, a diagnostic platform may estimate the similarity between retinas captured in different images based on the pattern of detectable defects (e.g., lesions, spots, etc.).

Initially, a diagnostic platform acquires a first image and accompanying first data that specifies at least one attribute of a first diagnostic session (step 801). In some embodiments, the first data accompanies the first image in the form of metadata (e.g., as part of a structured image format, such as DICOM, JPEG, etc.). In other embodiments, the first data is separately acquired by the diagnostic platform (e.g., from a different source than the first image). The diagnostic platform can then apply a classification model to the first image to produce a first characterization of an attribute of a first individual included in the first image (step 802). Step 802 of FIG. 8 may be largely similar to step 604 of FIG. 6 and step 703 of FIG. 7. The diagnostic platform can also populate a first record to associate the first image and the first characterization with at least a portion of the accompanying first data (step 803). Thus, the diagnostic platform can programmatically link the first characterization to the first image and/or the first data.

The diagnostic platform can then acquire, at some later point in time, a second image and accompanying second data that specifies at least one attribute of a second diagnostic session (step 804). The diagnostic platform can apply the same classification model to the second image to produce a second characterization of the attribute of a second individual included in the second image (step 805). Step 805 of FIG. 8 may be largely similar to step 802 of FIG. 8.

Thereafter, the diagnostic platform can compare the first and second characterizations of the attribute to determine the likelihood that the first and second individuals are the same individual (step 805). In some embodiments, the attribute is one of multiple attributes that are evaluated to assess similarity. For example, the diagnostic platform may determine whether the first and second individuals have comparable/consistent genders, ages, health conditions, etc.

If the diagnostic platform discovers that the first and second individuals are different people, then the diagnostic platform can populate a second record to associate the second image and the second characterization with at least a portion of the accompanying second data. In such a scenario, the first and second records will remain completely unrelated. However, in some instances, the diagnostic platform may discover that the first and second individuals are the same person (step 807). In such embodiments, the diagnostic platform can populate a second record to associate the second image with the first image (step 808). By associating images of the same person with each other, the diagnostic platform can readily produce a historical record of the health state of the body part under examination.

The diagnostic platform may also apply a degeneration model to the first image to produce a third image that includes one or more imperfections designed to simulate degeneration (e.g., of the retina). In such embodiments, the diagnostic platform may apply the classification model to the third image to produce a third characterization of the attribute. Such action causes the diagnostic platform to compare the second image to a version of the first image that has been modified to account for expected changes in the health state. By comparing the second and third characterizations of the attribute, the diagnostic platform can improve the likelihood of accurately determining whether the first and second individuals are the same person.

In some embodiments, the diagnostic platform may only acquire the first and second images. Thus, the diagnostic platform may never acquire the accompanying first and second data. In such embodiments, the diagnostic platform can apply the classification model to the first and second images as described above. However, the first record will only associate the first characterization of the attribute with the first image and the second record will only associate the second characterization of the attribute with the second image. Consequently, when the diagnostic platform determines whether the individuals included in the first and second images are the same individual, it will do so based solely on the pixel data corresponding to the first and second images.

Unless contrary to physical possibility, it is envisioned that the steps described above may be performed in various sequences and combinations. For example, the diagnostic platform may cause the image to be displayed on an interface to facilitate the rendering of a diagnosis by an individual. Such action may be performed contemporaneous with alerting the individual that a potential discrepancy in an attribute exists (e.g., through the surfacing of a notification).

Other steps may also be included in some embodiments. For example, the diagnostic platform may access a database associated with an enterprise involved in the diagnostic session, such as a hospital, clinic, etc. The database may include profiles associated with subjects involved in diagnostic sessions. By interfacing with the database, the diagnostic platform may be able to derive information from a profile associated with a given subject, and then use this information to assess validity of an image. For example, the diagnostic platform may apply a classification model to pixel data to a given image to produce a first characterization of an attribute associated with a subject (e.g., gender, age, health status). To produce a second characterization of the attribute, the diagnostic platform may parse the information included in a profile for the subject that is maintained by the hospital where the diagnostic session occurred.

Processing System

Figure 9:
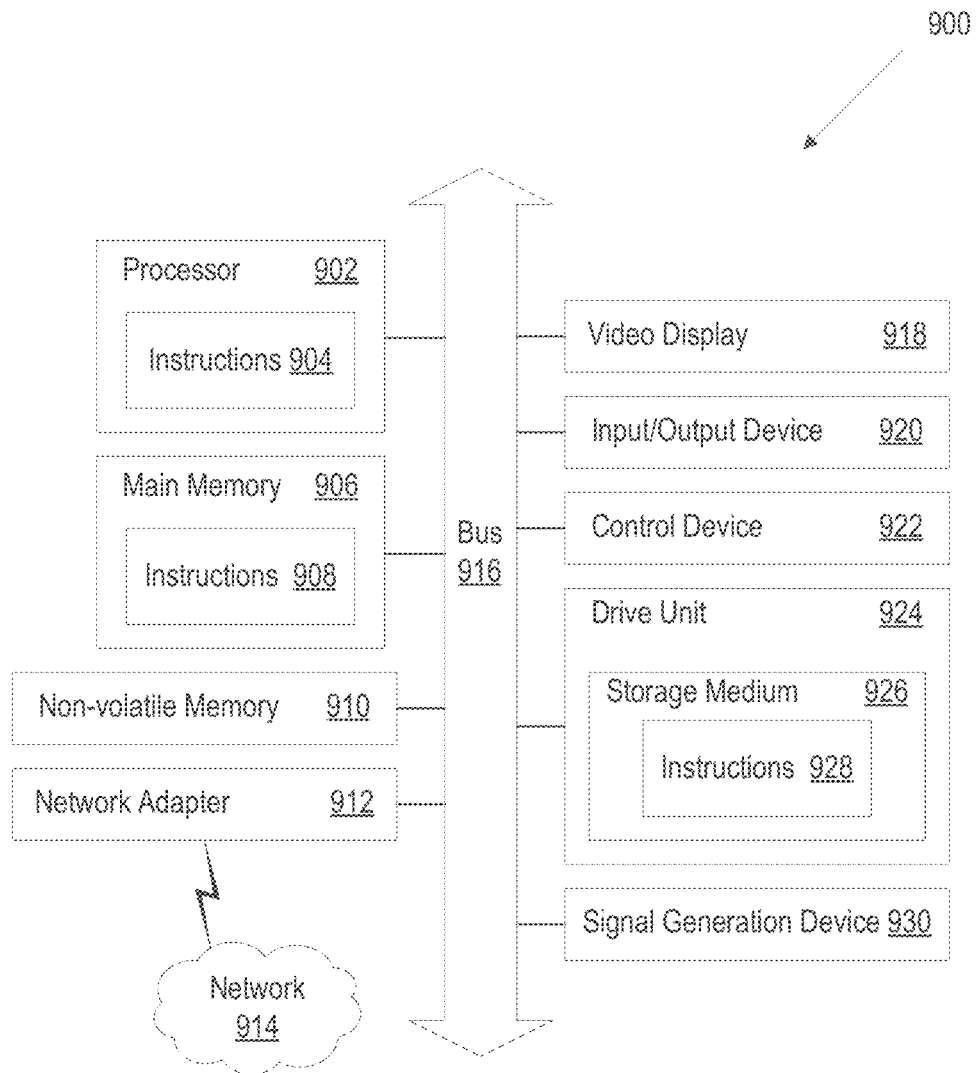
FIG. 9 is a block diagram illustrating an example of a processing system in which at least some operations described herein can be implemented.

FIG. 9 is a block diagram illustrating an example of a processing system 900 in which at least some operations described herein can be implemented. For example, some components of the processing system 900 may be hosted on a computing device that includes a diagnostic platform (e.g., diagnostic platform 302 of FIG. 3).

The processing system 900 may include one or more central processing units ("processors") 902, main memory 906, non-volatile memory 910, network adapter 912 (e.g., network interface), video display 918, input/output devices 920, control device 922 (e.g., keyboard and pointing devices), drive unit 924 including a storage medium 926, and signal generation device 930 that are communicatively connected to a bus 916. The bus 916 is illustrated as an abstraction that represents one or more physical buses and/or point-to-point connections that are connected by appropriate bridges, adapters, or controllers. The bus 916, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 900 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 900.

While the main memory 906, non-volatile memory 910, and storage medium 926 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 928. The term "machine-readable medium" and "storage medium" shall also be taken to include any medium that is capable of storing, encoding, or carrying a set of instructions for execution by the processing system 900.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 904, 908, 928) set at various times in various memory and storage devices in a computing device. When read and executed by the one or more processors 902, the instruction(s) cause the processing system 900 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 910, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 912 enables the processing system 900 to mediate data in a network 914 with an entity that is external to the processing system 900 through any communication protocol supported by the processing system 900 and the external entity. The network adapter 912 can include a network adaptor card, a wireless network interface card, a router, an access point, a wireless router, a switch, a multi-layer switch, a protocol converter, a gateway, a bridge, bridge router, a hub, a digital media receiver, and/or a repeater.

The network adapter 912 may include a firewall that governs and/or manages permission to access/proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A computer-implemented method comprising:
   acquiring, by a processor, a Digital Imaging and Communications in Medicine (DICOM) data object that includes
      pixel data corresponding to an image generated during a diagnostic session, and
      context data specifying an attribute of the diagnostic session;
   parsing, by the processor, the context data to establish a first characterization of the attribute;
   selecting, by the processor based on the attribute, a classification model from a library of classification models;
   applying, by the processor, the classification model to the pixel data to produce a second characterization of the attribute;
   comparing, by the processor, the first and second characterizations of the attribute;
   computing, by the processor, a degree of similarity between the first and second characterizations of the attribute,
      wherein a higher degree of similarity corresponds to a higher likelihood that the first and second characterizations of the attribute are substantially identical; and
   based on a comparison of the degree of similarity to a threshold, generating, by the processor, a notification that indicates a potential discrepancy in the attribute, as separately determined based on the pixel data and the context data, exists.

2. The computer-implemented method of claim 1, wherein each classification model in the library of classification models is designed to produce a characterization of a distinct attribute when applied to image data, including the pixel data of the DICOM data object.

3. The computer-implemented method of claim 1, wherein the attribute is associated with an individual captured in the image.

4. The computer-implemented method of claim 1, wherein the attribute is associated with a camera responsible for capturing the image.

5. A computer-implemented method comprising:
   acquiring, by a processor, a data object that includes
      pixel data corresponding to an image generated during a diagnostic session, and
      context data specifying an attribute of the diagnostic session;
   applying, by the processor, a classification model to the pixel data to produce a first characterization of the attribute;
   comparing, by the processor, the first characterization of the attribute to a second characterization of the attribute determined based on the context data, information provided by an individual as part of the diagnostic session, or any combination thereof;
   estimating, by the processor, a degree of consistency between the first and second characterizations of the attribute; and
   performing, by the processor, an action based on the degree of consistency.

6. The computer-implemented method of claim 5, wherein the data object is formatted according to a medical image standard.

7. The computer-implemented method of claim 5, wherein said performing comprises:
   responsive to a determination that the degree of consistency falls beneath a lower threshold,
      causing, by the processor, display of a notification that specifies a potential discrepancy in the attribute exists.

8. The computer-implemented method of claim 7, wherein the individual is a medical professional responsible for managing the diagnostic session, and wherein the method further comprises:
   displaying, by the processor, the image to facilitate the rendering of a diagnosis by the individual,
      wherein said displaying is performed contemporaneous with said causing to alert the individual of the potential discrepancy.

9. The computer-implemented method of claim 5, wherein said performing comprises:
   responsive to a determination that the degree of consistency falls beneath a lower threshold,
      identifying, by the processor, a potential discrepancy in a record associated with the data object; and
      storing, by the processor, the record in a log, the log specifying which images require further review to address potential discrepancies.

10. The computer-implemented method of claim 5, wherein said performing comprises:
    responsive to a determination that the degree of consistency exceeds an upper threshold,
       specifying, by the processor, in a record associated with the data object that no potential discrepancy was discovered.

11. The computer-implemented method of claim 5, wherein the data object is a Digital Imaging and Communications in Medicine (DICOM) data object.

12. The computer-implemented method of claim 5, wherein a lower degree of similarity corresponds to a lower likelihood that the first and second characterizations of the attribute are substantially identical, thereby indicating that the pixel data and either the context data or the information correspond to different diagnostic sessions, different cameras, or different subjects.

13. The computer-implemented method of claim 5, wherein the attribute is associated with a subject included in the image, and wherein the attribute is representative of:
whether the image is of a left eye or a right eye;
whether the image is of an exterior surface of an eye or an interior surface of the eye;
whether the subject is male or female; or
an age of the subject.

14. The computer-implemented method of claim 5, wherein the attribute is associated with a camera responsible for generating the image, and wherein the attribute is representative of:
a field of view;
a digital effect in the image that is indicative of a given camera model; or
a model of the camera.

15. The computer-implemented method of claim 5, wherein the classification model is a binary classification model, and wherein said comparing results in a determination as to whether the first and second characterizations are an exact match.

16. The computer-implemented method of claim 5, wherein the individual is a medical professional responsible for managing the diagnostic session.

17. The computer-implemented method of claim 5, wherein the individual is a subject captured in the image.

18. The computer-implemented method of claim 5, further comprising:
accessing, by the processor, a database associated with an enterprise involved in the diagnostic session,
wherein the database includes profiles associated with subjects involved in diagnostic sessions; and
deriving, by the processor, the information from a profile associated with a subject included in the image.

19. The computer-implemented method of claim 5, further comprising:
selecting, by the processor based on the attribute, the classification model from a library of classification models,
wherein each classification model in the library of classification models is designed to produce a characterization of a different attribute when applied to pixel data.

20. An electronic device comprising:
a memory that includes instructions for cross-checking information acquired from multiple sources to confirm the information is related to a single diagnostic session,
wherein the instructions, when executed by a processor, cause the processor to:
acquire a data object that includes
pixel data corresponding to an image generated during a diagnostic session, and
context data specifying an attribute of the diagnostic session;
parse the context data to identify a first characterization of the attribute;
apply a classification model to the pixel data to produce a second characterization of the attribute;
acquire information provided by an individual as part of the diagnostic session;
parse the information to identify a third characterization of the attribute;
estimate a degree of consistency between the first, second, and third characterizations of the attribute; and
perform an action based on the degree of consistency.

21. The electronic device of claim 20, wherein the classification model is a binary classification model, and wherein said estimating comprises determining whether the first, second, and third characterizations are substantially identical.

22. A non-transitory computer-readable medium with instructions stored thereon that, when executed by a processor, cause the processor to perform operations comprising:
acquiring a first image and accompanying first data that specifies at least one attribute of a first diagnostic session;
applying a classification model to the first image to produce a first characterization of an attribute of a first individual captured in the first image;
populating a first record to associate the first image and the first characterization with at least a portion of the accompanying first data;
acquiring a second image and accompanying second data that specifies at least one attribute of a second diagnostic session;
applying the classification model to the second image to produce a second characterization of the attribute of a second individual captured in the second image;
comparing the first and second characterizations of the feature to determine whether the first and second individuals are the same person; and
responsive to determining that the first and second individuals are the same person,
populating a second record to associate the second image with the first image.

23. The non-transitory computer-readable medium of claim 22, wherein the first and second images are retinal images.

24. The non-transitory computer-readable medium of claim 23, wherein the operations further comprise:
applying a degeneration model to the first image to produce a third image that includes one or more imperfections that were introduced to simulate retinal degradation; and
applying the classification model to the third image to produce a third characterization of the feature; and
comparing the second and third characterizations of the feature to determine whether the first and second individuals are the same person.

25. The non-transitory computer-readable medium of claim 22, wherein the operations further comprise:
generating a profile that includes the first and second images,
wherein the profile catalogues changes in a health state of the person over time.

* * * * *